United States Patent
Vig et al.

(10) Patent No.: US 7,176,308 B2
(45) Date of Patent: Feb. 13, 2007

(54) PROCESSES FOR PREPARING NOVEL METHYLENE BLUE DERIVATIVE

(75) Inventors: Rakesh Vig, Durham, CT (US); Scott Gerger, Des Moines, IA (US); Richard H. Selinfreund, Guilford, CT (US); Peter Miller, New London, CT (US); Mike Cunningham, Rochester, NY (US); Chris Phillips, Charlestown, RI (US); Ewell Cook, Colchester, CT (US); Anthony A. Saglimbeni, Deep River, CT (US)

(73) Assignee: Verification Technologies, Inc., Essex, CT (US)

( * ) Notice: Subject to any disclaimer, the term of this patent is extended or adjusted under 35 U.S.C. 154(b) by 0 days.

(21) Appl. No.: 10/715,226

(22) Filed: Nov. 17, 2003

(65) Prior Publication Data

US 2005/0107607 A1  May 19, 2005

Related U.S. Application Data

(63) Continuation-in-part of application No. 10/715,244, filed on Nov. 17, 2003, which is a continuation-in-part of application No. 10/641,784, filed on Aug. 15, 2003, now Pat. No. 6,952,392, which is a continuation-in-part of application No. 10/418,898, filed on Apr. 17, 2003.

(60) Provisional application No. 60/393,397, filed on Jul. 2, 2002, provisional application No. 60/391,857, filed on Jun. 26, 2002, provisional application No. 60/391,773, filed on Jun. 25, 2002, provisional application No. 60/390,647, filed on Jun. 21, 2002, provisional application No. 60/389,223, filed on Jun. 17, 2002.

(51) Int. Cl.
*C07D 279/34* (2006.01)
*C07D 279/18* (2006.01)

(52) U.S. Cl. .......................................... 544/37; 544/36

(58) Field of Classification Search .................. 544/37
See application file for complete search history.

(56) References Cited

U.S. PATENT DOCUMENTS

| | | | |
|---|---|---|---|
| 5,815,484 A | 9/1998 | Smith et al. | |
| 5,963,536 A | 10/1999 | Schneck et al. | |
| 6,011,772 A | 1/2000 | Rollhaus et al. | |
| 6,228,440 B1 | 5/2001 | Dailey et al. | |
| 6,338,933 B1 | 1/2002 | Lawandy et al. | |
| 6,589,626 B2 | 7/2003 | Selinfreund et al. | |
| 6,638,593 B2 | 10/2003 | Selinfreund et al. | |
| 6,641,886 B1 | 11/2003 | Bakos et al. | |
| 6,733,950 B2 | 5/2004 | Breitung et al. | |
| 6,756,103 B2 | 6/2004 | Thompson et al. | |
| 2002/0067674 A1 | 6/2002 | Schneck et al. | |
| 2003/0219124 A1 | 11/2003 | Selinfreund et al. | |
| 2004/0004922 A1 | 1/2004 | Selinfreund et al. | |
| 2004/0110088 A1 | 6/2004 | Vig et al. | |
| 2004/0121262 A1 | 6/2004 | Selinfreund et al. | |
| 2004/0152017 A1 | 8/2004 | Vig et al. | |
| 2005/0107607 A1 | 5/2005 | Vig et al. | |

FOREIGN PATENT DOCUMENTS

| | | |
|---|---|---|
| JP | 01-228976 A | 9/1989 |
| JP | 08-1228836 A | 5/1996 |
| WO | WO 98/0818 | 2/1998 |
| WO | WO 02/03386 A2 | 1/2002 |

OTHER PUBLICATIONS

Mellish et al. (Photochemistry and Photobiology, 2002, 75(4): 392-397).*
Kenneth Taylor Journal of Histochemistry and Cytochemistry (1960), 8, 248-57.*
J. Daneke and H.W. Wanzlick, Liebigs Ann. Chem. 740, pp. 52-62 (1970).
Strekowski, et al., "A Synthetic Rout to 3-(dialkylamino)phenothiazin-5-ium salts . . . ," J. Heterocyclic Chem., vol. 30(6) pp. 1693-1695 (1993).
Chandra, et al., "Studies on Some New Phenothiazines," Can. J. Chem., (1967) vol. 45, pp. 761-767.
Saraf, et al., "Recent Advances in the Synthesis of Phenothiazines," Hetrocycles, (1987) vol. 26 (1), pp. 239-273.
Cauquil, et al., "No 195-Recherches dans la serie de la . . . " Bull. Sco. Chim. France, (1955) pp. 1061-1075.
Daneke, et al., "Addition von Nucleophilen an in situ erzeugtes Phenazithionium Kation," Liebigs Ann. Chem., vol. 740, pp. 52-62 (1970).
Morrison & Boyd, "Organic Chemistry," Third Edition (1973), p. 360.

* cited by examiner

*Primary Examiner*—Kahsay Habte
(74) *Attorney, Agent, or Firm*—Kelley Drye & Warren LLP

(57) ABSTRACT

Methods for the preparation of 7-(dipropylamino)phenothiazin-3-ylidene]-dipropylamine.

3 Claims, 6 Drawing Sheets

PROCESSES FOR PREPARING NOVEL METHYLENE BLUE DERIVATIVE

RELATED APPLICATIONS

This application is a continuation-in-part application of U.S. patent application Ser. No. 10/715,244 filed Nov. 17, 2003 which is a continuation-in-part application of U.S. patent application Ser. No. 10/641,784 filed Aug. 15, 2003 now U.S. Pat. No. 6,952,392 which is a continuation-in-part of U.S. patent application Ser. No. 10/418,898 filed Apr. 17, 2003 which claims priority to U.S. Provisional Patent Application Nos. 60/389,223 filed Jun. 17, 2002, 60/390,647 filed Jun. 21, 2002, 60/391,773 filed Jun. 25, 2002, 60/391,857 filed Jun. 26, 2002, and 60/393,397 filed Jul. 2, 2002, the disclosure of each which is herein incorporated by reference.

BACKGROUND OF THE INVENTION

1. Field of the Invention

The present invention generally relates to transient optical state change security materials reactive to a wavelength of about 630 nm to about 660 nm, in particular to wavelengths produced by DVD optical readers, and which further may be made reactive to the wavelengths produced by CD optical readers. More particularly, the present invention discloses a bis-propyl amine analog of methylene blue and composition useful as such a transient optical state change security material. Such materials may be used by directed application to optical medium to effectuate copy-protection. More specifically, the materials may be used to manufacture optically readable digital storage medium that protects the information stored thereon from being copied using conventional optical medium readers, but permits reading of the information from the digital storage media by the same readers.

2. Description of the Related Art

Data is stored on optical media in the form of optical deformations or marks placed at discrete locations in one or more layers of the medium. Such deformations or marks effectuate changes in light reflectivity. To read the data on an optical medium, an optical medium player or reader is used. An optical medium player or reader conventionally shines a small spot of laser light, the "readout" spot, through the disc substrate onto the data layer containing such optical deformations or marks as the medium or laser head rotates. Two common types of optical media are the CD disc, providing a maximum storage space of about 650 megabytes of data on a single-side (SS), single-layer (SL) disc, and the DVD disc providing about 4.37 GB (1 GB=$2^{31}$ bytes) on a single-sided (SS), single-layer (SL) disc. The ECMA Technical Committee TC31 was established in 1984 for the standardization of Optical Discs and Optical Disc Cartridges, making contributions to ISO/IEC SC23 with respect to International Standards.

The vast majority of commercially-available software, video, audio, and entertainment pieces available today are recorded in read-only optical format. One reason for this is that data replication onto read-only optical formats is significantly cheaper than data replication onto writable and rewritable optical formats. Another reason is that read-only formats are less problematic from a reading reliability standpoint. For example, some CD readers/players have trouble reading CD-R media, which has a lower reflectivity, and thus requires a higher-powered reading laser, or one that is better "tuned" to a specific wavelength.

In conventional "read-only" type optical media (e.g., "CD-ROM"), data is generally encoded by a series of pits and lands that are metallized. A readout spot directed from the non-metallized side is reflected in a manner that the light of readout spot is reflected back into a photosensor in the reader. When referenced from the laser reading side, pits are technically referred to as bumps. The transitions between pits and lands, and the timing in between such transitions, represent channel bits. Thus the pit and lands in themselves are not representations of a sequence of zeros or ones. Typically, in CDs 14 channel bits make up a data symbol that translates to an 8 bit data value, in a process referred to as 8 to 14 modulation (EFM). DVD uses a modified version of EFM, known as EFM+ to convert 8-bit data directly into 16 channel bits. The NRZI (non-return to zero inverted) waveform representation is used to interpret the binary sequence on the disc.

Microscopic pits formed in the surface of the plastic medium are arranged in tracks, conventionally spaced radially from the center hub in a spiral track originating at the medium center hub and ending toward the medium's outer rim. The pitted side of the medium is conventionally coated with a reflectance layer such as a thin layer of aluminum or gold. The "pits" as seen from the metallized side, are also referred to "bumps" when referencing view from the laser-read side. A lacquer layer is typically coated on the pit side as a protective layer.

The intensity of the light reflected from a read-only medium's surface measured by an optical medium player or reader varies according to the presence or absence of pits along the information track. As defect-induced errors may interfere with read, all optical discs employ error management strategies to eliminate the effect of such errors.

The optical reader, such as the CD or DVD reader, has the job of finding and reading the data stored as bumps on the disc. In a conventional player a drive motor spins the disc. A laser and lens system focus light on the bumps, and an optical pickup head (PUH) receives reflected light. A tracking mechanism moves the laser assembly so that the laser's beam can follow the spiral track, conventionally moving the laser outward from the center as the disc is played. As the laser moves outward from the center of the disc, the bumps move past the laser faster, as the speed of the bumps is equal to the radius times the speed at which the disc is revolving (rpm). A spindle motor is conventionally employed to slow the speed of the disc when the laser is reading further and further out from the center of the disc permitting the laser to read at a constant speed, such that the data is read from the disc at a constant speed.

The semiconductor laser utilized, the spread of its wavelength, and its operational temperature affect the wavelength read by the pick up head (PUH) of the reader. DVD readers presently utilize lasers that produce a wavelength of about 630 to about 660 nm, with standard DVD readers measuring a wavelength of 650±5 nm and standard DVD-R readers measuring a wavelength of 650+10/−5 nm. As would be understood by one of skill in the art, the PUHs can detect only those reflected beams that fall within a certain angular deviation from the incident beam. For example, a typical DVD-R requires that the radial deviation be no more than ±0.80° and tangential deviation no more than ±0.30°.

Optical media of all types have greatly reduced the manufacturing costs involved in selling content such as software, video and audio works, and games, due to their small size and the relatively inexpensive amount of resources involved in their production. They have also unfortunately improved the economics of the pirate, and in some media, such as video and audio, have permitted significantly better pirated-copies to be sold to the general public than permitted with other data storage media. Media distributors report the loss of billions of dollars of potential sales due to high quality copies.

Typically, a pirate makes an optical master by extracting logic data from the optical medium, copying it onto a magnetic tape, and setting the tape on a mastering apparatus. Pirates also sometimes use CD or DVD recordable medium duplicator equipment to make copies of a distributed medium, which duplicated copies can be sold directly or used as pre-masters for creating a new glass master for replication. Hundreds of thousands of pirated optical media can be pressed from a single master with no degradation in the quality of the information stored on the optical media. As consumer demand for optical media remains high, and because such medium is easily reproduced at a low cost, counterfeiting has become prevalent.

WO 02/03386 A2, which asserts common inventors to the present application, discloses methods for preventing copying of data from an optical storage media by detecting optical dis-uniformities or changes on the disc, and/or changes in readout signal upon re-reading of a particular area on the optical storage medium, in particular those caused by light-sensitive materials, such as dyes, which may affect the readout wavelength by absorbing, reflecting, refracting or otherwise affecting the incident beam. Software control may be used to deny access to content if the dis-uniformity or change in read signal is not detected at the position on the disc wherein the dis-uniformity or change is anticipated. The disclosure of WO 02/03386 A2 is incorporated herein in its entirety by reference.

A preferred embodiment described in publication WO 02/03386 A2 comprises light-sensitive materials are optically-changeable security materials that are positioned upon the optical disc in a manner that they do not adversely affect the data-read of the readout signal in one optical state but upon exposure to the wavelength of the optical reader incident beam covert to a second optical state, preferably in a time-delayed fashion, that does affect the data-read of the readout signal. In a preferred embodiment described in WO 02/03386 A2, the optically-changeable security material only transiently changes optical state and its optical state reverts over time.

It has been discovered by the present inventors that the optimal characteristics for such preferred transient optically-changeable security materials described in publication WO 02/03386 A2 depend upon a number of factors, including, the characteristics of the incident beam generated by the laser reader used (such as the beam intensity and wavelength), the particular materials used to fabricate the optical disc in particular with respect to the optical characteristics of such materials with respect to the reading beam (such as refractive index and birefringence), the particular formatting of the disc (such as pit depth), where the optically-changeable security material is positioned on or within the disc (e.g., on the surface versus in a layer of the disc/in the data section of the disc versus), the optical characteristics of other materials that may be introduced to effectuate incorporation of the optically-changeable security material onto or into the disc, the characteristics of the pickup head (PUH) of the optical reader in particular with respect to readout wavelength and angle of deviation permitted for pickup of reflected light emanating from the incident beam, the reading characteristics of the optical reader system in particular related to scan velocity, the time for re-scan, and rotational speed of the disc. For example, the material should not change state too quickly so as not to allow the PUH to observe both states. On the other hand, it should not change state too slowly so as to eventuate in a disc that would take non-commercially acceptable times for validation of the disc and read.

Unexpectedly the present inventors have also discovered that the dye composition can effectuate a lambda shift, in particular a red shift, if the dye molecules aggregate in the coating. For example, methylene blue which has an absorption at 650 in aqueous medium, is found to absorb at 600 nm in a typical DVD coating. Aggregation may be caused by the stereochemical structure of the dye substance utilized. The effect of the dye system on the overall coating thickness has also been unexpectedly found to affect jitter, wobble and playback fidelity of an optical disc.

An optimal transient optical state change security material should be thermally and photochemically stable under conditions of optical use and at ambient conditions for a significant period of time. It should be soluble in a matrix that comprises the disc, or that can be adheredly-applied to the disc. An optimal transient optical state change security material should revert to its state without the need for extraneous inputs of energy, and should demonstrate a change in optical state at the incident wavelength of the reader.

There is a need for optical state change security materials that may be employed in a manner described in WO 02/03386 A2 to effectuate copy-protection of optical discs, in particular DVDs and CDs, that conform to ISO/IEC standards when read by their respective ISO/IEC standardized readers. In particular there is a need for identifying materials that may be used in such copy protection methodologies without requiring modification to optical medium readers.

DEFINITIONS

"Data Deformation": a structural perturbation on or in an item that represents stored data and can be read by an optical reader.

"Dye": an organic material detectable by optical means.

"Fabry-Perot Interferometer": an Interferometer making use of multiple reflections between two closely spaced reflective surfaces, and typically has a resolvance of $\lambda/\Delta\lambda = m \, r/1-r$ "Interferometer": a device employing two or more reflective surfaces to split a beam of light coming from a single source into two or more light beams which are later combined so as to interfere in a constructive or destructive manner with each other.

"Optical Medium": a medium of any geometric shape (not necessarily circular) that is capable of storing digital data that may be read by an optical reader.

"Optical Reader": a Reader (as defined below) for the reading of Optical Medium.

"Optical State Change Security Material": refers to an inorganic or organic material used to authenticate, identify or protect an Optical Medium by changing optical state from a first optical state to a second optical state.

"Permanent Optical State Change Security Material": refers to a Transient Optical State Change Security Material that undergoes change in optical state for more than thirty times upon read of the Optical Medium by an Optical Reader.

"Reader": any device capable of detecting data that has been recorded on an optical medium. By the term "reader" it is meant to include, without limitation, a player. Examples are CD and DVD readers.

"Read-only Optical Medium": an Optical Medium that has digital data represented in a series of pits and lands.

"Recording Layer": a section of an optical medium where the data is recorded for reading, playing or uploading to a computer. Such data may include software programs, software data, audio files and video files.

"Re-read": reading a portion of the data recorded on a medium after it has been initially read.

"Transient Optical State Change Security Material": refers to an inorganic or organic material used to authenticate, identify or protect an Optical Medium by transiently changing optical state between a first optical sate and a second optical state and that may undergo such change in optical state more than one time upon read of the Optical Medium by an Optical Reader in a manner detectable by such Optical Reader.

"Temporary Optical State Change Security Material": refers to an Optical State Change Security Material that undergoes change in optical state for less than thirty times upon read of the Optical Medium by an Optical Reader.

For the purpose of the rest of the disclosure it is understood that the terms as defined above are intended whether such terms are in all initial cap, or not.

SUMMARY OF THE INVENTION

The present invention provides a dye and dye systems which make use of dye substances that do not shift appreciably with respect to activation wavelengths when placed within the coating of an optical disc. One preferred dye and dye system comprises a bis-propylamine analog of methylene blue. Processes for making such dye and dye composition are herein disclosed.

Such dye and dye systems may be optimized to exhibit a reversible change in optical state which is detectable by a reader upon exposure of such dyes and dye systems, in particular to a wavelength of about 630 to about 670 nm. Preferably such dye and dye systems are applied in a manner to result in a transient optical state change security material, providing for a change in optical state that can be repeated numerous times upon exposure to/and removal from such wavelength.

In one preferred dye system embodiment, the dye system on an optical disc comprises: (1) a dye that rapidly changes optical state from a first unactivated optical state to a second activated optical state in response to a wavelength of about 630 to about 660 nm which is detectable by the uptake head of an optical reader when the dye is in its second optical state, but not the dye is in its first optical state; (2) a dye-carrying polymer in which the dye is dispersed; and (3) a material that aids in reducing the reversal time of the dye from its second activated optical state back to its first unactivated optical state. Optionally such system may also comprise a material that aids in reducing the time to the second activated optical state from the first unactivated optical state. The optical state change in any optically measurable manner, for example in causing a change in reflection and/or refraction, as long as the optical change can be detected. For example, in one embodiment the dye/dye system changes the percent reflectance on the optical disc by approximately 25% to approximately 30% which has been seen to be sufficient for detection at the pickup head.

One particularly useful class of dyes capable of being activated by a wavelength of about 630 nm to about 660 nm that have been identified are:

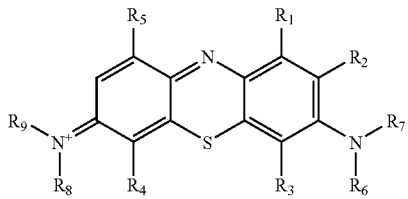

where $R_6$, $R_7$, $R_8$, and $R_9$ are alkyl and $R_1$, $R_2$, $R_3$, $R_4$ and $R_5$ are selected from the group consisting of hydrogen, alkyl, aryl, alkoxy, thioalkoxy, alkylamino, nitro, amino and halogen. In one preferred embodiment $R_6$, $R_7$, $R_8$, and $R_9$ are each, or independently, propyl or hexyl and $R_1$, $R_2$, $R_3$, $R_4$ and $R_5$ are hydrogen or alkyl.

Such dye substances can be incorporated into a dye system which comprises an electron donor agent (ED)/electron transfer agent (ETA). Such compounds are electron rich and provide electrons to the dye molecule for example when the dye molecule is reduced to the corresponding leuco form. In the presence of laser light, this phenomenon may be referred to as photoreduction.

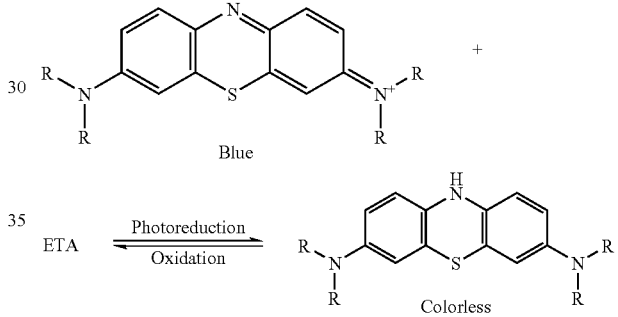

Non-limiting examples of ETAs which may be incorporated into the dye system include triethanol amine, diethanol amine, TMG, DMEA, DEMEA, TMED, EDTA, Bis-Tris, p-tolylimido diethanol, N-tert-butyldiethanol amine, 4-morpholine ethanol, 1,4-bis-2-hydroxyethyl piperazine, bicine, BES, 3-Pyrrolidino-1,2-propanediol, 1-Amino-3,3-diethoxypropane, (S)-3-tert-Butylamino-1,2-propanediol, DL-Isoproterenol sulfate dihydrate, N,N-Bis(2-hydroxyethyl)-3-methoxyaniline, 1,1'-[[3-(Dimethylamino)propyl]imino]bis-2-propanol, Triethanolamine Ethoxylate, 2,2'-(4-Methylphenylimino)diethanol, Triisopropanolamine, 2-[[2-[2-(dimethylamino)ethoxy]ethyl]methylamino]ethanol, Triethanolamine Hydrochloride, N-phenyldiethanolamine, 1-[N,N-Bis(2-hydroxyethyl) amino]-2-propanol, N-t-Butyldiethanolamine, N-Butyldiethanolamine, 3-Morpholino-1,2-propanediol, N,N-Bis(2-hydroxyethyl)ethylenediamine, 3-(Diethylamino)-1,2-propane-diol, 4-(3-hydroxypropyl) morpholine, N-Ethyldiethanolamine, 4-(2-Hydroxyethyl)-morpholine, N-Methyldiethanolamine, 3-morphonlino-1,2-propanediol, 3-diisopropyl-amino-1,2-propanediol, 3-(dimethylamino)-1,2-propanediol, 3-piperidino-1,2-propanediol, 3-(diethylamino)-1,2-propanediol, dropropizine. The ETA may be incorporated into the polymeric base of a dye system physically or chemically. For example, a useful ETA may be bound to the repeating polymeric unit. For example, a compound of the following structure has been found to be a useful ETA:

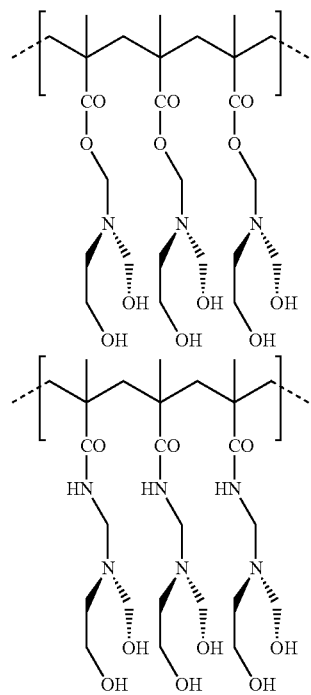

as well as other compounds comprising a polymer having a bis(2-hydroxy ethyl) amino functionality. A preferred polymer may be in the molecular weight range of 50–100 k.

Other non-oxygen associated ETAs may be used, such as a combination of reductants such as Fe (II)–Fe (III).

A bis-propyl amine analog of methylene blue, [7-(dipropylamino)phenothiazin-3-ylidene]dipropylamine, referenced herein a propylene blue, has been found to be a particularly useful dye substance, in particular in conjunction with other components in a dye system, as described below, which can be used to effectively transiently convert from one optical state to another optical state upon exposure to the read beam of a DVD reader in a manner that is detectable by the read beam of the reader.

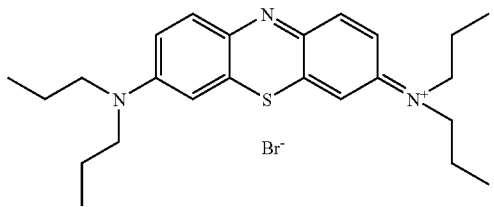

Such compound is believed to be unknown in the art.

The dye and/or dye system may be used on an optical disc to effectuate data changes on the disc, preferably at the bit level code. As described in the applications referenced above, a security software can be sued to confirm the change in code. The dye/dye system is preferably placed in a manner on the disc so as not to alter playability on industry compliant DVD devices.

In one embodiment, propylene blue is prepared by introducing dipropylamine functionalities into phenothiazine at C-3 and C-7 of the ring structure. In another embodiment propylene blue is prepared by treating phenothiazine with dipropylamine in the presence of bromine. In another embodiment, phenothiazine is treated with bromine followed by reaction with dipropylamine, optionally in the presence of copper. In yet another embodiment of the invention, phenothiazine is first nitrosylated, then intermediate then acetylated to protect the central nitrogen, the resulting intermediate reduced to the diamine, and the reduced product subsequently alkylated. In an alternative process, two aromatic components are combined to generate the central thiazine ring, such as reacting (4-aminophenyl)dipropylamine with [2-amino-5-(diproylamino)phenyl]thiosulfonic acid. In yet another alternative synthetic scheme (4-{[4-(dipropylamino)phenyl]amino}phenyl)dipropylamine is reacted in the presence of S, $I_2$, DCB to give propylene blue. Synthesis schemes and methods of purification are set forth in more detail in the detailed description below.

BRIEF DESCRIPTION OF THE DRAWINGS

The accompanying drawings, which are incorporated in and constitute part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
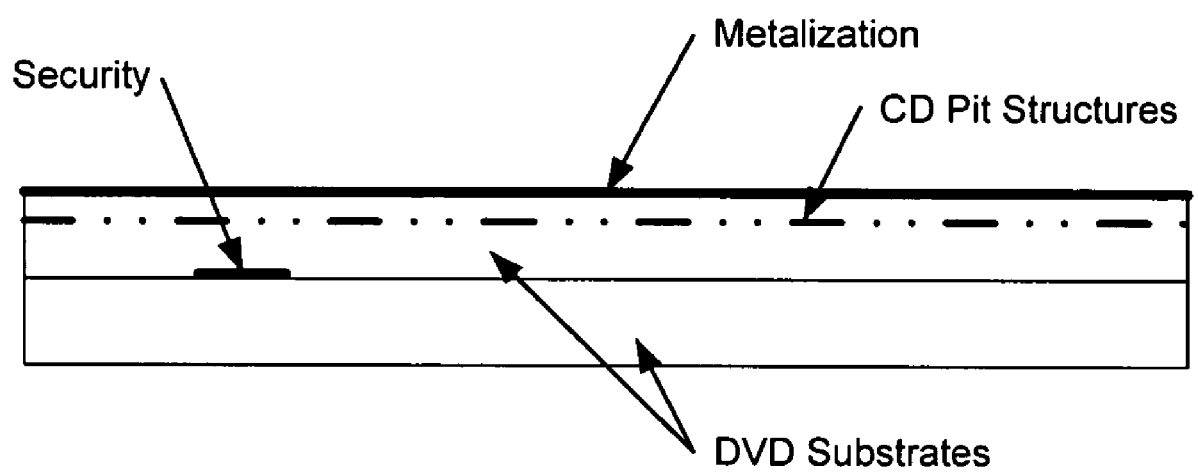
FIG. 1 illustrates a multi-layer optical disc embodiment of the present invention having reflective layer, dye layer, and transparent substrate.

The present invention provides for transient optical state change security materials reactive to a wavelength of about 630 nm to about 660 nm, in particular to wavelengths produced by DVD optical readers. The transient optical state change security materials may be used to manufacture optically readable digital storage medium that protects the information stored thereon from being copied using conventional optical medium readers, but permits reading of the information from the digital storage media by the same readers.

As disclosed in WO 02/03386 A2, which asserts common inventors to the present application, transient optical state change security materials may be used to effectuate copy-protection of an optical disc by providing a change in optical state upon activation of the material by the incident reading laser beam, that is of such character that upon a second read of the area of the disc where the transient optical state change security material is located a change in data read is detected at the optical pickup head. The materials may be used to cause an uncorrectable error upon re-read of such a character that the error interferes with copying function of most optical readers that require oversampling in the copying process, and/or a uncorrectable/correctable error, or a change in interpretation of a data read, that due to an algorithm on the disc, which may be incorporated as an encryption code, and/or an algorithm incorporated into the reader and/or component associated with the reader, is used to authenticate the disc and permit copying only upon authentication.

The materials may also be used to effectuate complementary data sequences (CDSs) both of which are interpreted as valid, both of which are interpreted as erroneous, or one of which is interpreted as valid and the other as erroneous, or one of which is interpreted as erroneous and the other as valid. That is, the for example, the materials may be used to cause a pit to disappear altogether of change its length because part of it disappeared. It is preferred that the material be conformal with the data structure. Copy protection may be effected using CDSs by, for example, having the first valid data read attributable to the material in its unactivated state directing the reader to an erroneous track on the disc, while having the second valid data read attributable to the material in its activated state directing the reader to the correct track for further effectuating of the read. As would be understood, copying of the disc in such situation is hampered by resampling by the copying device (which reads two different valid data reads). When such error is detected, re-seek algorithms internal to the drive will cause the data stored in the tracking control to be re-read. If the transient optical state change security material, which may be temporary or permanent, is in its second state, and the second state is selected as to allow the underlying data to be read, the new address will be correct and the content on the disc will be able to be read. In one embodiment of such "spoofing" technique for copy-protection, the material is placed at the subcode level in the lead-in zone thus effecting the table of contents. The material may be placed at the microlevel in the CRC field. A copy of the disc incorporating data having the first valid data read alone would not work due to the failure of the data to direct subsequent reading to the correct track. The transient optical state change security material may also provide for a valid data state read in a first optical state, but an uncorrectable read error in a second optical state, making it significantly more difficult for a would-be copier of the disc to reproduce an operable disc by incorporating an uncorrectable error, such as a physical deformation, into the disc.

By "correctable error" it is meant an error which is correctable by the ECC used with respect to the optical disc system, while an "uncorrectable error" is an error which is not correctable. ECC are algorithms that attempt to correct errors due to manufacturing defects such that the opticaldisc works as intended. Error detection methods are conventionally based on the concept of parity. All optical discs employ error management strategies to eliminate the effect of defect-induced errors. It has been found that even with the most careful handling, it is difficult to consistently manufacture optical discs in which the defect-induced error rate is less than $10^{-6}$. Optical recording systems are typically designed to handle a bit-error rate in the range of $10^{-5}$ to $10^{-4}$. The size of the defect influences the degree of error associated with the defect. Thus some defects create such a marginal signal disturbance that the data are almost always decoded correctly. Slightly smaller defects might induce errors hardly ever. Macro or micro depositions may also be used to cause correctable or uncorrectable errors. For example, micro depositions may be of such size as to kill a data group that is fixable by $C_1/C_2$ of ECC of a CD, but if applied to kill enough groups may cause an uncorrectable error detectable by such software.

The type of transient perturbation that is desired to be effectuated, whether a correctable error, uncorrectable error, two or more complementary valid data sequences, a valid data sequence and a corresponding invalid data sequence and/or other detectable change at the optical pickup head, will dictate where on the disc the transient optical state change security material will be placed. For example, if a data change detectable by the optical pickup head is desired, the material should not of course be placed in the clamping zone. If there is a valid to valid, or erroneous to erroneous data state change, in order to allow easy detection it is preferred that the data state change causes a change in the values read. In error state to error state changes the level of severity of the errors preferably is different, thereby aiding detectability.

The present invention discloses transient optical state change security materials (both temporary optical state change materials, and permanent optical state change security materials) that change optical state upon exposure to a wavelength produced by DVD readers. The material, which may comprise a dye or dye stem, transiently changes the signal read by the pickup head by changing, for example the reflectivity of the laser beam when the material is in its activated state versus its unactivated state. Typically, when used for the production of copy protected optical discs, the dye acts to change a detectable parameter, e.g. reflectivity, at a few selected pit/land structures. A typical dye system comprises a dye which changes from a first unactivated optical state to a second activated optical state upon exposure to a wavelength produced by a DVD reader, e.g. from about 630 to about 660 nm, an electron donor agent or electron transfer agent which aids in the conversion to the activated second optical state from the unactivated first optical state, and a polymer. It has been found that the system composition affects the laser activation, the rate and intensity of optical state change in response to an activation wavelength, and the conformal application of the dye/electron donor to the disc.

A DVD read laser has a spectra centered about 650 nm wavelength. The absorption spectra for methylene blue in solution shows an absorption maxima at 655 nm. While such dye might appear to be useful in itself as a transient optical state change material, when applied to optical disc it was observed that the absorption underwent a bathochromic shift with the spectrum having an absorption maxima at about 590 nm due to aggregation. The absorption spectrum was of the compound was found to be modifiable by altering the steric bulk on the nitrogen. A preferred structure in regard to a a methylene blue backbone comprised improved electron withdrawal at the positively charged side chain nitrogen, and electron withdrawal at the other side chain nitrogen.

One particularly useful class of dyes capable of being activated by a wavelength of about 630 nm to about 660 nm that have been identified are:

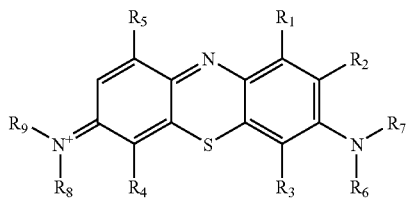

where $R_6$, $R_7$, $R_8$, and $R_9$ are alky and $R_1$, $R_2$, $R_3$, $R_4$ and $R_5$ are selected from the group consisting of hydrogen, alkyl, aryl, alkoxy, thioalkoxy, alkylamino, nitro, amino and halogen. In one preferred embodiment $R_6$, $R_7$, $R_8$, and $R_9$ are each, or independently, propyl or hexyl and $R_1$, $R_2$, $R_3$, $R_4$ and $R_5$ are hydrogen or alkyl.

Preparation of Exemplar Thiazine Compounds Useful for Copy-Protected DVDs

EXAMPLE 1

Propyl and Hexyl Analogs of Methylene Blue

To shift the absorption maxima closer to 650 nm, propyl (MB-3) and hexyl (MB-6) analogs of methylene blue were synthesized using the procedure described by Mellish et al. as set forth below.

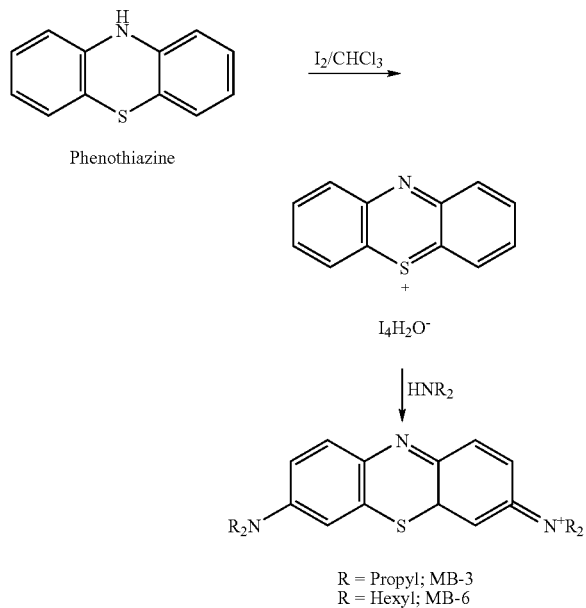

The absorption maxima of the compounds when coated onto optical media was in the expected range and the change in optical state was detectable by the PUH. The optical density of 5% poly-HEMA (poly-2-hydroxyethyl methacrylate), 250 mg MB-3, and 160 mg Bis-Tris (2,2-Bis(hydroxymethyl)-2-2',2"-nitroethanol) on one disc was 0.22 absorbance units at 650 nm and the optical density on another disc using 325 mg MB-3, 5% poly-HEMA and 160 mg Bis-Tris was 0.3 absorbance units. The disc with optical density of 0.22 absorbance units demonstrated about a 18% photobleach at 650 nm. The disc with optical density 0.32 absorbance units demonstrated about a 30% photobleach at 650 nm.

An ETA or ED (electron donor agent) is a compound that is electron rich and provides electrons to the dye molecule that is being reduced to the corresponding leuco form. In the presence of laser light, this phenomenon is called photoreduction:

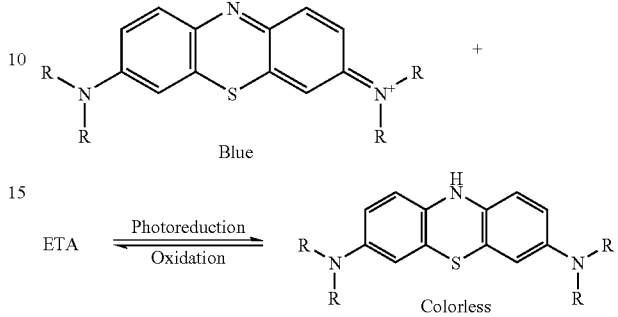

ETAs are particularly useful in a dye system of the present invention when photoreduction is a principle means of optical state change back to the activated state. ETA's that can be used in this system include, but not limited to, triethanol amine, diethanol amine, TMG, DMEA, DEMEA, TMED, EDTA, Bis-Tris, p-tolylimido diethanol, N-tert-butyldiethanol amine, 4-morpholine ethanol, 1,4-bis2-hydroxyethyl piperazine, bicine, BES, 3-Pyrrolidino-1,2-propanediol, 1-Amino-3,3-diethoxypropane, (S)-3-tert-Butylamino -1,2-propanediol, DL-Isoproterenol sulfate dihydrate, N,N-Bis(2-hydroxyethyl)-3-methoxyaniline, 1,1'-[[3-(Dimethylamino)propyl]imino]bis-2-propanol, Triethanolamine Ethoxylate, 2,2'-(4-Methylphenylimino)diethanol, Triisopropanolamine, 2-[[2-[2-dimethylamino)ethoxy]ethyl]methylamino]ethanol, TriethanolamineHydrochloride, N -phenyldiethanolamine, 1-[N,N-Bis(2-hydroxyethyl)amino]2-propanol, N-t-Butyldi-ethanolamine, N-Butyldiethanolamine, 3-Morpholino-1,2-propanediol, N,N-Bis(2-hydroxyethyl)ethylenediamine, 3-(Diethylamino)-1,2-propanediol, 4-(3-hydroxypropyl) morpholine, N-Ethyldiethanolamine, 4-(2-Hydroxyethyl)morpholine, N-methyldiethanol-amine, 3-morphonlino-1,2-propanediol, 3-diisopropylamino-1,2-propanediol, 3-(dimethyl-amino)-1,2-propanediol, 3-piperidino-1,2-propanediol and 3-(diethylamino)-1,2-propanediol, dropropizine. Such ETAs have been found to photobleach the system using a DVD laser on the pulsetec. In general percent photobleach observed was directly proportional to the amount of ETA added in the system, but it was found that there is a limit to the amount of ETA that can be tolerated in the system after which discs are not playable.

Preparation of Exemplar Copy-Protected DVD

EXAMPLE 2

Optical Disc Having Dye System Comprising MB-3

250 mg of MB-3 dye was added to a 25 ml 4% polymer solution in 1-methoxy 2-propanol Aldrich catalog No. 484407 and 150 mg of Bis-Tris was added. The resulting solution was stirred vigorously on a shaker for 30–60 min. The final solution was filtered through a 0.2 μm filter and was used to spin coat optical discs. The spin coater used for this purpose was model P-6708D manufactured by Specialty Coating Systems.

EXAMPLE 3

Optical Disc Having Dye System Comprising MB-3

To a 25 ml solution of 4% PolyHEMA in methoxy propanol was added 300 mg of MB-3 and 150 mg of Bis-Tris. The solution was stirred on a shaker for 30 min and filtered through 0.2 um filter and the filtered solution was used to coat discs using a spin coater Disc No. 1854-1857.

EXAMPLE 4

Optical Disc Having Dye System Comprising MB-3 and Poly HEMA

To 24.5 ml of methoxy propanol was added a 0.5 ml solution of 10% PolyHEMA in methoxy propanol, 250 mg of MB-3 and 100 mg of Bis-Tris. The solution was stirred on a shaker for 30 min and filtered through 0.2 um filter and filtered solution was used to coat discs using spin coater Disc No. SE1600-1611, 1625-1630, 1650-1652, 1687-1689, 1700-1726, 1750-1773, 1775-1786, 1825-1827, 1850-1852, 1875-1895.

EXAMPLE 5

Optical Disc Having Dye System Comprising MB-3 and 40% Hydrolysed PVA

To 24.5 ml of methoxy propanol was added a 0.5 ml solution of 10% 40% hydrolysed PVA in methoxy propanol, 250 mg of MB-3 and 100 mg of Bis-Tris. The solution was stirred on a shaker for 30 min and filtered through 0.2 um filter and filtered solution was used to coat discs using spin coater Disc No. SE1856-1858.

A two component dye system is yet another embodiment of the invention. In such system, the ETA is combined chemically with the polymer. It has been found by the present inventors that polymers that have ETA appended will photobleach. Useful electron transfer polymers include, but are not limited to: a) any polymer containing the bis(2-hydoxyethyl)amino functionality as shown below, b) homo-polymers or copolymers with vinyl acetate or methacrylate containing the (2-hydoxyethyl)amino functionality.

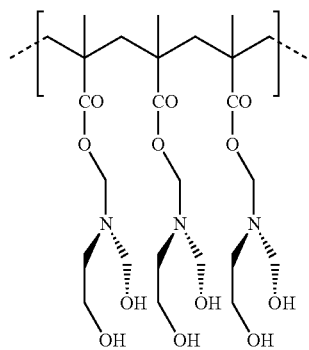

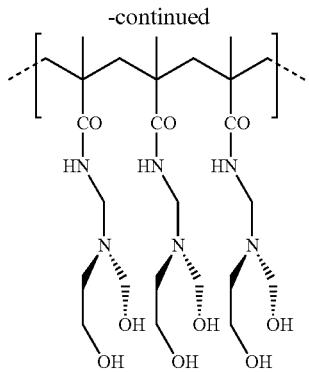

and c) any other polymer in Mol wt. range 50–100K that is soluble in methoxy propanol and having a bis(2-hydroxy ethyl) amino functionality.

EXAMPLE 6

ETA Polymer-Methylene Blue Dye System

Polyethylenimine which was 80% ethoxylated in water was adjusted to a pH of about 8 using concentrated HCl and methylene blue added to bring the absorbance to 3. Photobleach of the system was seen with a simple overhead projector to be in the range of 2–3 seconds with oxidation back to unactivated state in approximately 2–3 minutes.

Combinations of reductants such as Fe (II)–Fe (III) can be used for an oxygen free system. For example, the catalytic effect of ferrous ion on the photochemical bleaching of thionine in the presence of diethylallylthiourea is related to the present work on methylene blue. On irradiating a 0.001% aq. solution of thionine containing 0.0075 mol. per liter, the dye bleaches in 1–2 sec. The color returns again in 1–2 sec. after removal of the light. Similarly the leuco form of the dye will return to the original colored form in the presence of weak-strong oxidizing agents such as bromine or silver halides to name a few.

A useful embodiment dye is [7-(dipropylamino)phenothiazin-3-ylidene]dipropyl-amine, referred to herein alternatively as MB-3 and propylene blue. Preparation of such compound may be undertaken by a number of synthetic routes.

EXAMPLE 7

Preparation of Propylene Blue by Reacting Phenothiazine with Dipropyl Amine

Propylene blue may be prepared by treating 1 molecular proportion of phenothiazine with about 2–15 moles of dipropyl amine, more preferably about 5–7 moles, in methyl alcohol and/or tetrahydrofuran at −20° C. to 10° C., more preferably −10° C. to 5° C., in the presence of about 2–10 moles of bromine, more preferably 3–5 moles. The resulting mixture may be stirred at ambient temperature for 3–24 hours, preferably 5–10 hours. The resulting mixture may then be evaporated to dryness. Residue may be taken up in dichloromethane washed with weak acidic solution in water to remove excess amine and the crude product may be purified using crystallization with methanol, ethanol, propanol, isopropanol, butanol, isobutanol, dichloromethane, chloroform, acetonitrile or methoxy propanol.

Phenothiazine (5 g, 25 mmol) was dissolved in a mixture of 30 ml of MeOH/30 ml THF, and the resultant mixture cooled to 0 degrees C in an ice bath. Dipropyl amine (24 ml, 175 mmol, 7 eq.) was poured into the reaction mixture, followed by drop wise addition of bromine (3.85 ml, 75 mmol, 3 eq.) over 15 to 20 minutes. After allowing stirring cold for a period of between 3–12 hours, the dark blue reaction mixture was evaporated to dryness. The residue was taken up in 400 ml of methylene chloride, washed 3× with 75 ml portions of 1N HCl, followed by 75 ml of saturated brine, dried with sodium sulfate, filtered and evaporated to yield 9.6 g of a dark blue glass. The crude product was stirred with 400 ml ethyl ether for 2–3 hours, and then scraped with a spatula until a filterable solid resulted. The crude powdered product was stirred for 2–3 hours more, and then filtered to yield 9.7 g of a purple-blue solid.

EXAMPLE 8

Purification of Propylene Blue of Example 7 Without Column Chromatography

Crude product (3 grams) of Example 7 is placed in a 500 ml round bottom flask equipped with a magnetic stir-bar and 150 ml of acetonitrile is added to it; the flask is fitted with a needle vented septum and the solution is heated/sonicated in a 70° C. sonicator until visibly dissolved (approximately 30 min). The resulting deep blue solution is then stirred on a magnetic stirrer until it cools to ambient temperature. When cool the solution is filtered through a glass-fritted funnel, and the flask is rinsed with minimum amount (15 ml) of acetonitrile to give 0.94 grams of a blue powder and a dark blue acetonitrile solution. The dark blue solution is transferred to a 200 ml round bottom flask (in portions) and concentrated in vacuo to give a deep purple foam/glass. The solid is then triturated with a 5% acetonitrile in ether. After stirring overnight, the sides of the flask are scratched with a metal spatula, and stirring is continued for an additional hour, as well as intermittent sonication in a room temperature sonicator. The resulting solution is filtered to provide a purple-waxy solid. The solid is dissolved in dichloromethane and concentrated in vacuo to provide a dark purple glass. Treatment in a similar manner with diethyl ether (stirring 30 min, scratching and stirring/sonication) provides about 1.6 gram of the dye as a dark purple crystal powder. This solid is about 30% purity by HPLC.

EXAMPLE 9

Purification of Propylene Blue of Example 7 With Column Chromatography

Crude material (5 g) from Example 7 is purified using column chromatography over 300 g of silica gel (80 mm diameter column) with a gradient solvent system beginning with methylene chloride, 2.5% MeOH, 5% MeOH in methylene chloride. A yellow impurity which is too faint to see on TLC elutes with the methylene chloride fraction, followed by a brown band when 2.5% MeOH is used. Two closely spaced blue dyes follow the brown band, the second of which is the desired product. The product containing fractions are combined and evaporated to a blue glass. The product is again stirred with x ml of ethyl ether, then scraped with a spatula and filtered to yield 2.3 g of dark purple-blue powder. TLC solvent system: 95/5 methylene chloride: methanol. The brown band has an $R_f$ of ~0.4, and the 2 blue products have $R_f$'s of 0.35 (impurity) and 0.32 (desired). This sample is found to be 75% pure HPLC.

EXAMPLE 10

Purification of Propylene Blue of Example 7 By Reduction to Leuco Form

The crude dyestuff of Example 7 may also be purified by reducing it to the leuco form with bisulfite, with oxygen preferably excluded. Conversion of the leuco form to the dyestuff may be performed by a mild oxidant (e.g., bromine or chlorine).

EXAMPLE 11

Preparation of Propylene Blue by Reacting Phenothiazine With Dipropyl Amine Followed by Precipitation of Zinc Salt 5 g of phenothiazine (25 mmol) is dissolved in a mixture of 30 ml of MeOH/30 ml THF, and the resulting mixture is cooled in an ice bath. Subsequently, 24 ml of dipropyl amine (175 mmol) is added to the reaction mixture and then 3.85 ml of bromine (75 mmol) is slowly added drop wise. Thereafter, the reaction mixture is stirred overnight at ambient temperature, the solvent being evaporated. The residue is dissolved in 100 ml of dichloromethane and washed with 1N HCl three times and with brine, and then is dried with sodium sulfate. After evaporating the solvent, the crude product is washed with ether and filtered to obtain a purple-blue solid. The crude product is then dissolved in hot water (200–400 ml) and filtered to remove insoluble matters. The hot filtrate is treated with 50% $ZnCl_2$ solution in water and then sodium chloride (30 g) to precipitate the $ZnCl_2$ double salt (2.0 g). The double salt is dissolved in 0.1 N NaOH solution (200 ml) and filtered to remove undissolved particles. The filtrate is washed with ether and treated with sodium chloride to precipitate the product. After filtering, the brown product is washed with ether until the washings are faint red color. The yield is about 0.5 g. The purity of the compound is about ~85% by HPLC.

EXAMPLE 12

Preparation of Propylene Blue by Reacting Phenothiazine With Dipropyl Amine Followed by Precipitation of Zinc Salt Propylene blue may be prepared by reacting (4-{[4-(dipropylamino)phenyl]amino}phenyl)dipropylamine:

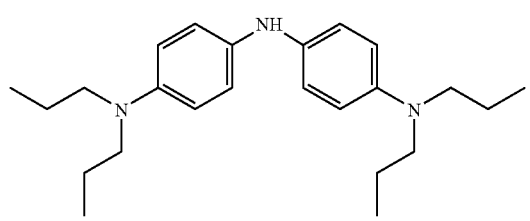

(4-{[4-(dipropylamino)phenyl]amino}phenyl)dipropylamine via the following reaction scheme:

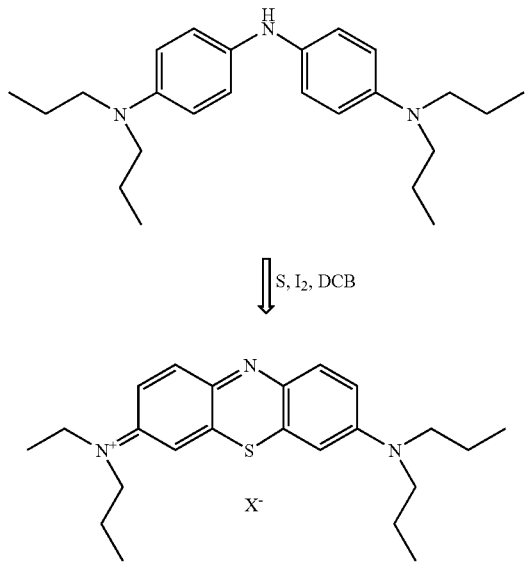

wherein X = Cl, Br, I

EXAMPLE 13

Preparation of Propylene Blue by Combining Aromatic Components

Propylene blue may alternatively be synthesized by reaction of (4-aminophenyl)dipropylamine with [2-amino-5-(dipropylamino)phenyl]thiosulfonic acid as set forth below:

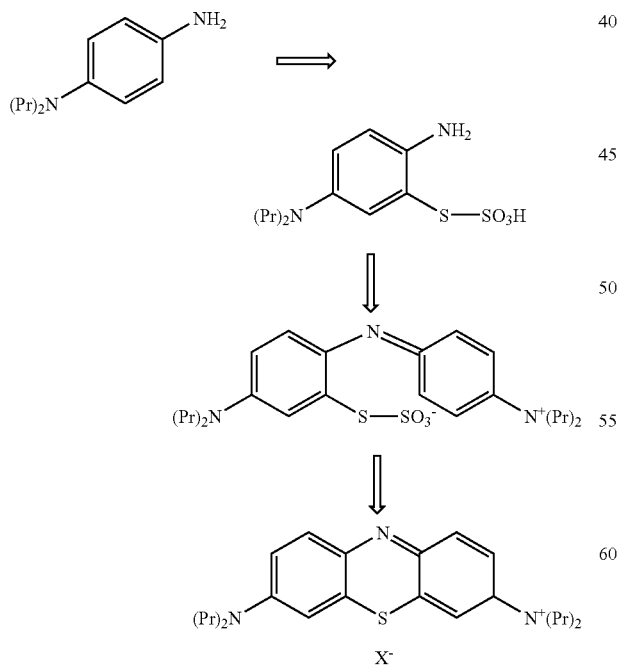

where X=Cl, Br, I

EXAMPLE 14

Preparation of Propylene Blue through Dibromophenothiazine

Propylene blue may also be synthesized from:

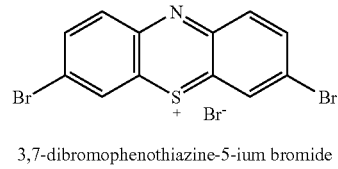

3,7-dibromophenothiazine-5-ium bromide which may be obtained by reacting phenothiazine with bromine, or may be obtained commercially through Aldrich. The 3,7-dibromophenothiazine-5-ium bromide may then be reacted with the appropriate dialkylamine, optionally in the presence of Cu, to obtain the propylene blue.

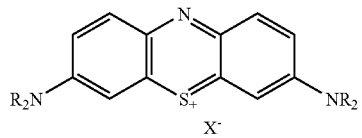

EXAMPLE 15

Preparation of Propylene Blue through Dibromophenothiazine

The phenothiazine may also be nitrated to form:

3,7-dinitrophenothiazine

The central nitrogen of the phenothiazine derivative may then be protected with acetyl, followed by reduction, using for example Zn/HOAc. Alkylation of the resultant intermediate with an alkyl bromide and base in boiling methylisobutyl ketone or with an aliphatic aldehyde plus NaBH$_3$CN should give after mild hydrolysis the leuco form of propylene blue.

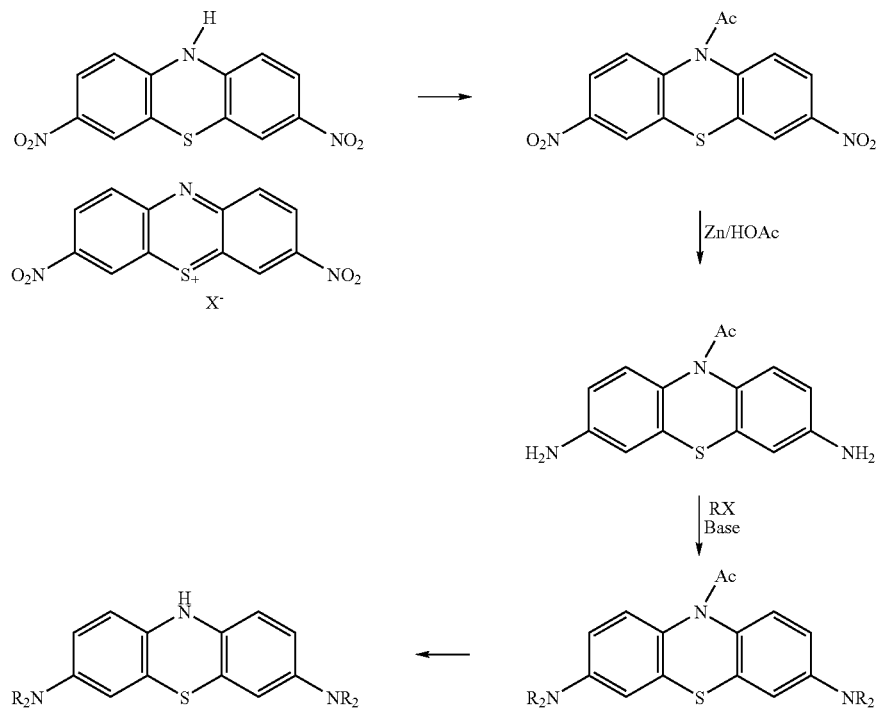

Figure 2:
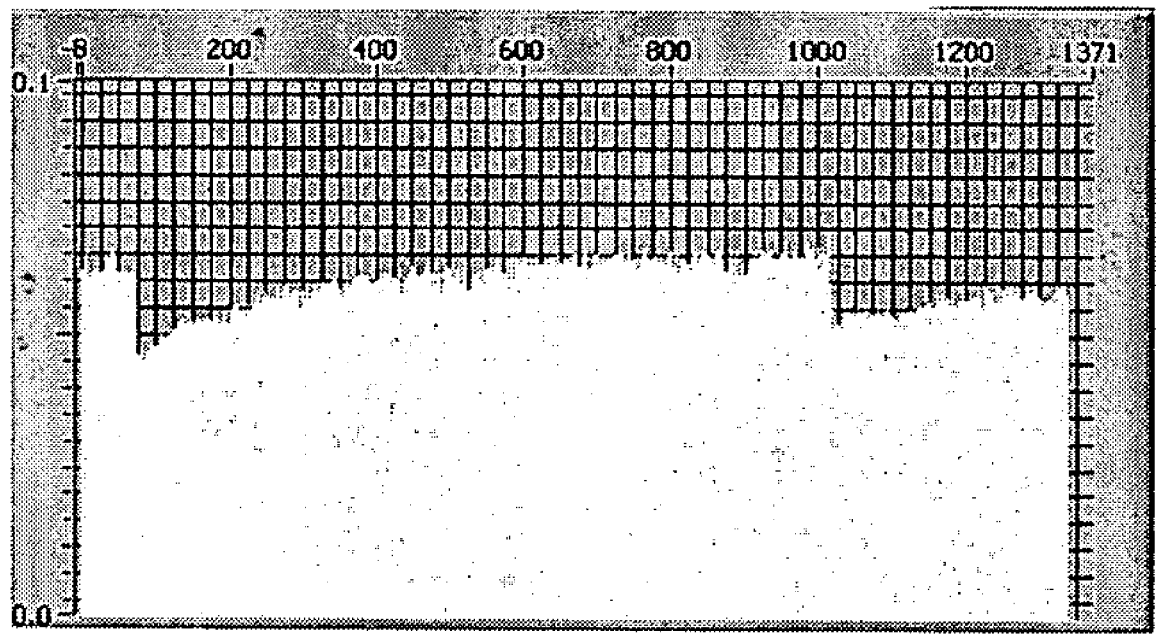
FIG. 2 is a chart of reflectivity versus time in regard to a dye system unexposed to DVD reader laser light, exposed to DVD reader laser light, and recovered from exposure to DVD reader laser light.
Figure 3:
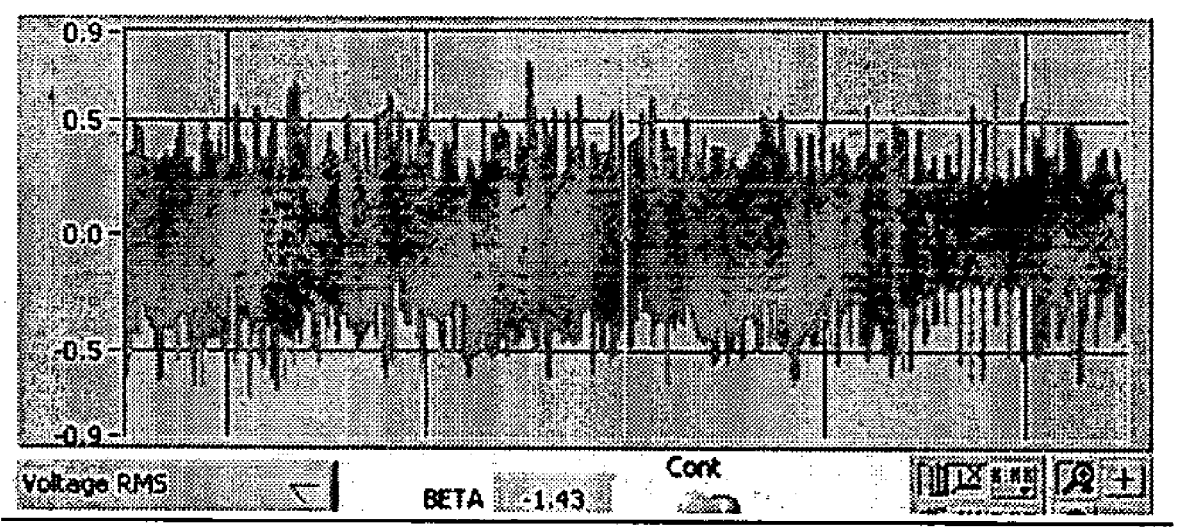
FIG. 3 is a real time plot of pit/land signal with respect to the dye system of FIG. 2.
Figure 4:
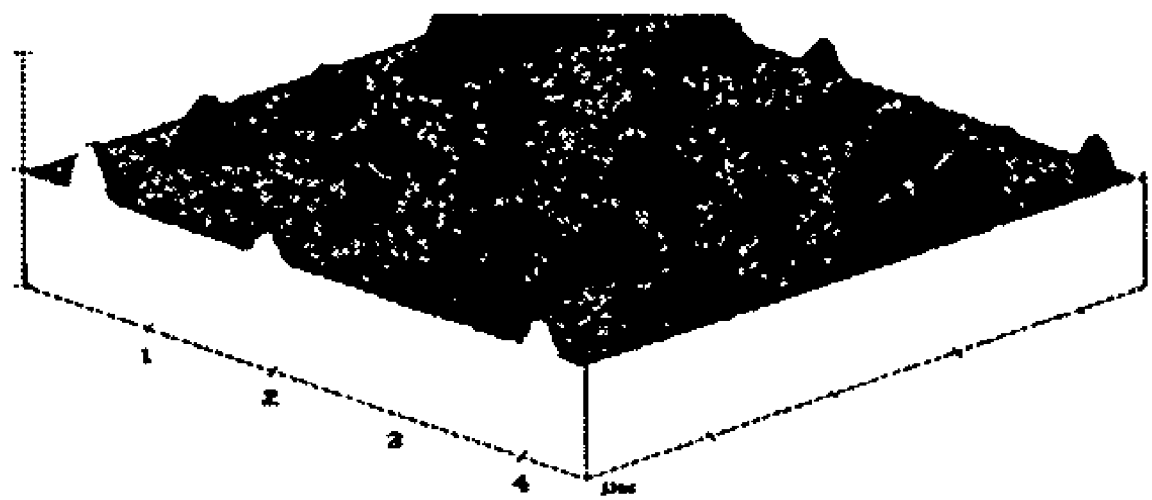
FIG. 4 is an atomic force microscope photo of a multi-depth pit master which may be used to form a multi-depth pit disc.
Figure 5:
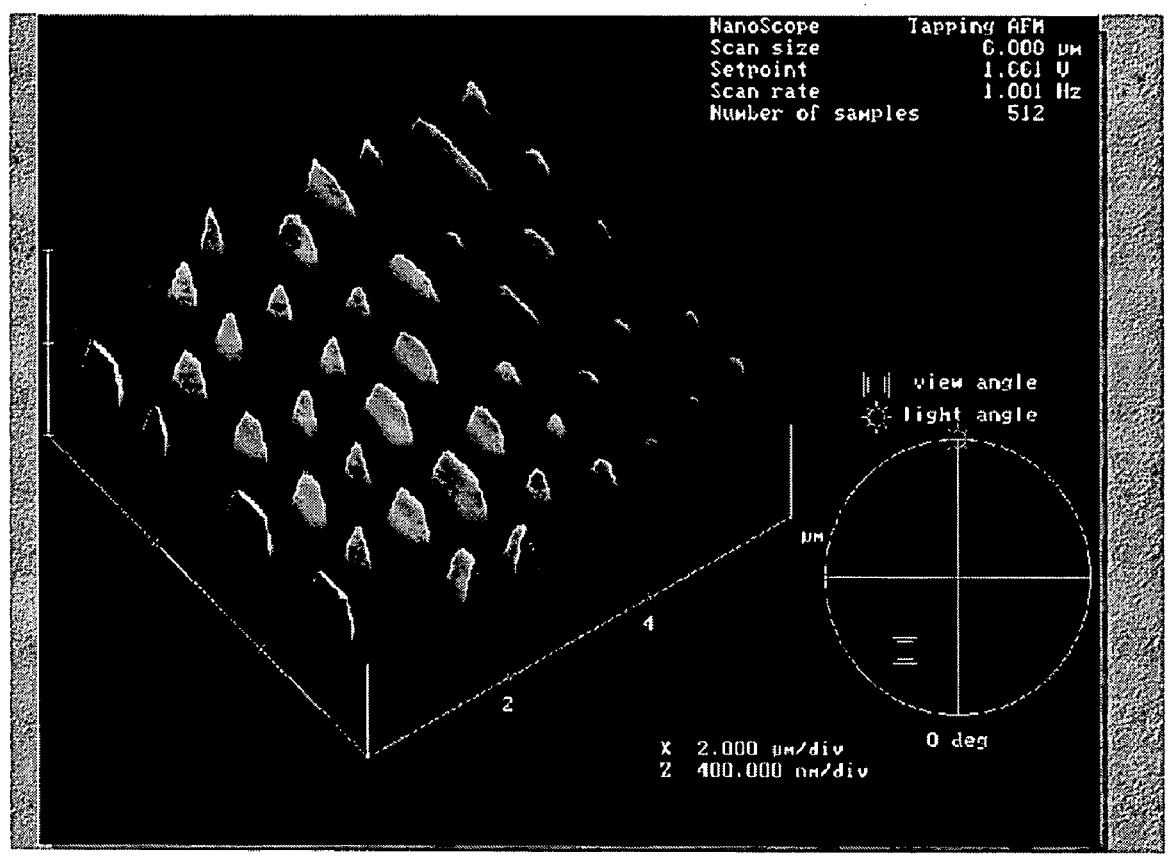
FIG. 5 is an atomic force microscope photo of a multi-depth pit disc with dye/dye system of the present invention being coated on the highest bumps (deepest pits).

Now turning to the figures, FIG. 1 illustrates a cross-section of an optical medium embodiment comprising a transient optical state change security material between two substrates. FIG. 4 is an atomic force microscope photo of a multi-depth pit master which may be used to form a multi-depth pit disc. Such multi-depth pit (i.e. heightened bump) may be useful for easing application of the dye to select pits (bumps from the read side). FIG. 5 is an atomic force microscope photo of an exemplar multi-depth pit disc with dye system of the present invention being coated on the highest bumps (deepest pits). FIG. 2 is a chart of reflectivity versus time in regard to a dye system before and during exposure to a DVD reader laser light, and after it has returned to the unactivated state. FIG. 3 is a real time plot of pit/land signal with respect to the dye system of FIG. 2.

Figure 6:
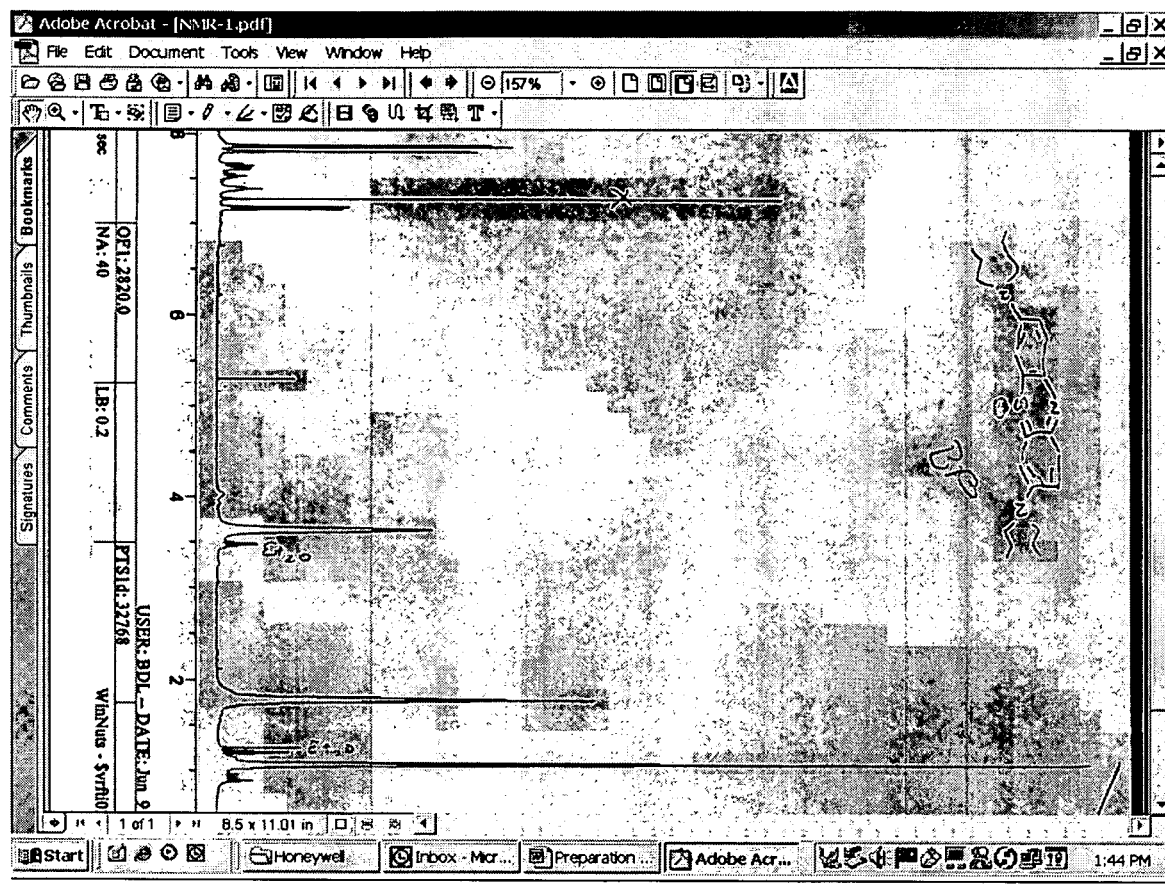
FIG. 6 is a NMR spectrum of propylene blue of the present invention.

FIG. 6 is a NMR spectrum of propylene blue of the present invention.

Optimization of transient optical state change security materials for a particular reader is influenced in part by the particular materials used to fabricate each layer of the optical disc itself, and the material's position vis-à-vis such layers and the incident laser beam. It is therefore useful when selecting for such optimal security materials with respect to a particular reader that the material be placed on a disc of similar fabrication and placed for testing purposes in a manner similar to how they are ultimately to be placed.

Placement of Transient Optical State Change Security Materials with Respect to Optical Data Structures on the Optical Discs In General As disclosed in WO 02/03386 A2, the transient optical state change security materials may be placed anywhere on or within the optical medium so long the PUH can detect the change in optical state. Such security materials may advantageously be placed in or on the optical medium on either the laser incident surface ("LI Method") or the pit/land surface (a.k.a. the focal plane) of the optical medium ("FP Method"). Advantageously, changes in reflectivity, absorbance, optical clarity, and birefringence due to the application of the security materials may be monitored to assure that such materials do not interfere with industry standards, suggestive that the optical medium might not adequately perform in its reader. Audio Development's CD-CATS and DVD-CATS testers may be used to measure servo responses, HF signal amplitudes, and error behaviors.

Surface Application

The transient optical state change security materials may be applied topically to a surface of the optical medium or component of the optical medium during manufacture. Topical surface application may be by any of the imprinting techniques known to those of ordinary skill in the art, including, but not limited, air brush, industrial ink jet printing, desktop ink jet printing, silkscreen printing, sponge/brush application, air brushing, gravure printing, offset lithography, oleophilic ink deposition onto a wetted surface.

The material may also be spin coated. Spin coating a layer comprising the transient optical state change security materials may be a preferred method of application due to precision and uniformity requirements. Only minor process modification are typically necessary to implement in-line deposition by spin coating. The spin coat may be applied using any means known to those of ordinary skill in the art. For example, a precise, small quantity of dye may be placed in a radial line with the disc stationary and the disc subsequently spun to produce a precisely coated area. Conventionally spin coating entails a first ramp of acceleration to first speed, a first dwell time at first speed, a second ramp of acceleration to second speed, a second dwell time at second speed, a third ramp of acceleration to third speed, a third dwell time at the third speed, deceleration, and post conditioning (baking/drying/curing at defined temperatures for defined periods of time) The spin profile may be advantageously controlled to produce the desired coating. It is preferred that when such security materials are placed on an otherwise exposed surface of the completed optical medium, that the security materials be coated to protect against wear of the security material due to handling of the optical medium. Thus, for example when security material is applied to the laser-incident surface of a completed optical disc, it is advantageous that a hard-coating be placed over the security material to prevent wear or removal of the security dye from such surface.

The transient optical state change security materials may be coated onto the pit-surface prior to lacquering of the optical medium, addition of a second substrate (DVD) and/or application of any label. The later addition of such materials helps protect against removal and degradation of the security material. Any covering over the security material may further comprise a special filtering material, such as GE filtering polycarbonate.

The transient optical state change security materials may be placed at the pit/land surface.

In one embodiment, pit/land placement may makes use of pit geometries needed to accommodate dye deposition at the focal plane of the disc. Techniques such as Atomic Force Microscopy (AFM) may be used to verify dimensions. Optimal pit geometries for the particular security material may be determined by spin coating the material onto a surface having variable pit depths, determining which pits contain the materials as by, for example, microscopy, and determining which pit dimensions which may hold material after spin coating, actually allow for playback without the dye in them, and without errors. The optical medium with the material and determined pit geometries is then checked to determine whether a dual data state, error to valid, or valid to error, may be produced. Different radii, depths etc. may be investigated.

For example, without any limitation, a variable pit depth glass master for a CD may be made using a 350 nm thick photoresist and LBR (laser bean recorder) power step series, as to form 13 steps in random order, except for nominal depth tracts which contain 50 MB of pseudo-random user data, as follows: 160 nm (nominal pit depth), 120 nm, 150 nm, 180 nm, 160 nm (nominal), 210 nm, 240 nm, 270 nm, 160 nm (nominal), 300 nm, 320 nm, 350 nm, 160 nm (nominal). Similarly, a variable pit depth master for DVD may be made using a 200 nm thick photoresist and LBR power step series, as to form 13 steps in random order except the nominal depth tracks, wherein each track contains 360 MB of pseudo-random user data, as follows: 105 nm (nominal), 80 nm, 95 nm, 110 nm, 105 nm (nominal), 125 nm, 140 nm, 155 nm, 105 nm, 170 nm, 185 nm, 200 nm, 105 nm (nominal). The discs can be spun coat with material comprising transient optical state change security material, the pit depths incorporating the material determined, and pits of such dimensions analyzed for whether the impact upon read without the material when the optical medium is completed (metallized, lacquered etc.)

Detection from the laser-read side may be enhanced by including one or more deep pits in the substrate, such pits being made using a master designed to form multiple-depth pits. Detection may also be improved by optimizing pit geometry of the deep pits. Variable pit depth glass masters may be fabricated. For example, 350 nm thick photoresists and LBR power step series may be employed to produce different steps including nominal depth tracks for pseudo-random user data The pits may advantageously be placed only in the outer 5 mm of the disc, or in the lead out region of the disc. In such case, only the outer portion of the disc, or lead out region, need be coated.

The deep pits may also be used to form an interferometer by placement of the security material with respect to the deep pit prior to metallization.

Placement of Transient Optical State Change Security Material in Polycarbonate with Formation of Extended Pits Upon Molding Prior to Metallization to Form an Interferometer Along the Extended Pits The transient optical state change security material may incorporated into the polycarbonate and deep pits (bumps from the read side) flanking one or more lands molded into the polycarbonate at predetermined locations. The pits may be constructed to be of such depth that as to form an interferometer between the enlarged bumps, when viewed from the read side, that fail to reflect sufficiently for read by the PUH of the optical reader when the security material changes state due exposure to the incident read laser beam. This system therefore employs two components: the transient optical state change security material distributed throughout the polycarbonate, and a interferometer, of the Fabry-Perot type ("FPI").

The FPI works by varying the amount of light reflected back to a source. This variation is dependent on the intensity, angle and wavelength of the light entering the interferometer. The physical construction of an FPI, when viewed from the read-side, can be effectuated during the stamping procedure by creating one or more pits of extended depth flanking one or more lands. The glass master advantageously is modified to create such pits of extended depth. The deep pits act as the walls of the FPI, while the reflective land at the bottom acts as the primary reflective surface. By carefully selecting the transient optical phase change security material, under one set of conditions (intensity, wavelength, angle) there will be considerable reflectivity back to the source, while under a second set of conditions, there will be significantly less light reflected back to the source. These two states will be driven by the security material placed in the polycarbonate (PC).

If the interferometer is appropriately manufactured, and the transient optical state change security material chosen, the material in the PC will be essentially transparent to the PUH and all data will be read at one state. During the read, the material will absorb energy. When enough energy has been absorbed by the material its transmittance will decrease (less energy passes through) and it will cause a slight change in refractive index. In the second state with the transmittance decreased, if property designed, the input energy threshold for the FPI can be made to be crossed, and very little signal will be reflected. By carefully selecting the security material and its concentration in the PC, one can cause enough signal to the optical data structures so as to be able to read such data. One the other hand, if RI is changed when the material is activated by the read beam, the security material and its concentration, and the depths of the pits (from the non-read side) should be such as to result in a change in wavelength that crosses the FPI threshold resulting in a reduction in reflectivity, but the wavelength change should be small enough that normal sized optical data structures may still be resolved. It should be noted that the disc may have to be preformatted, such as is the case with CD-RW, if the automatic gain control (AGC) is inappropriately invoked based on ATIP information.

Placement of Transient Optical State Change Security Material between Substrates Comprising the Optical Medium Dye may be deposited and encapsulated between substrates, for example an ambient protective polycarbonate, such as that produced by General Electric. Such placement eliminates optical hard coating, uses existing manufacturing processes, provides protection, and expands the possible dye chemistries that might be employed because read laser optical power density is, for example, greater at 0.6 mm from the pit surface than at 1.2 mm.

STATEMENT REGARDING PREFFRERED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

We claim:

1. A method of the synthesis of [7-dipropylamino) phenothiazin-3-ylidene]dipropylarnine comprising the step of reacting 3,7-dibromophenothiazine-5-ium bromide with dipropylamine in the presence of copper.

2. A method for isolating [7-dipropylamino) phenothiazin-3-ylidene]dipropylamine from an impure mixture comprising the steps of:
   (a) dissolving the impure mixture in hot water;
   (b) filtering the hot solution of step (a) to remove insoluble matters;
   (c) treating the hot filtrate of step (b) with $ZnCl_2$ to precipitate the $ZnCl_2$ salt;
   (d) dissolving the $ZnCl_2$ salt in a base;
   (a) washing the filtrate of step (d) with an organic solvent and treating the same with a salt to precipitate [7-dipropylamino) phenothiazin-3-ylidene]dipropylamine.

3. A method for the synthesis of [7-(dipropylamino) phcnothiazin-3-ylidene]dipropylamine comprising the step of reacting phenothiazine or any salt thereof with dipropyl amine in the presence of copper.

* * * * *